United States Patent
Chang et al.

(10) Patent No.: US 9,467,182 B2
(45) Date of Patent: Oct. 11, 2016

(54) SIGNAL DECOMPOSITION METHOD AND ELECTRONIC APPARATUS USING THE SAME

(71) Applicant: National Chiao Tung University, Hsinchu (TW)

(72) Inventors: Chia-Chi Chang, Hsinchu (TW); Tzu-Chien Hsiao, Hsinchu (TW); Hung-Yi Hsu, Taichung (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 14/724,828

(22) Filed: May 29, 2015

(65) Prior Publication Data

US 2016/0269064 A1 Sep. 15, 2016

(30) Foreign Application Priority Data

Mar. 12, 2015 (TW) .............................. 104107944 A

(51) Int. Cl.
*H04L 27/06* (2006.01)
*H04B 1/12* (2006.01)
*H04L 7/027* (2006.01)

(52) U.S. Cl.
CPC ............... *H04B 1/123* (2013.01); *H04L 7/027* (2013.01)

(58) Field of Classification Search
CPC ..... H04B 1/123; H04L 7/027; A61B 5/0452; A61B 5/726; A61B 5/04017; A61B 5/0402; A61B 5/0205; A61B 5/04014; A61B 5/048; A61B 5/7253; A61B 5/0006; A61B 5/021; A61B 5/04012; A61B 5/0432; A61B 5/04325; A61B 5/7239; A61B 5/725; A61B 5/7257; A61B 5/727

See application file for complete search history.

(56) References Cited

U.S. PATENT DOCUMENTS

| 6,738,734 B1 | 5/2004 | Huang |
| 6,862,558 B2 | 3/2005 | Huang |
| 7,359,749 B2* | 4/2008 | Quenet ................ A61B 5/0452 600/509 |
| 7,499,686 B2 | 3/2009 | Sinclair et al. |

(Continued)

OTHER PUBLICATIONS

A. Karagiannis and P. Constantinou, "Noise components identification in biomedical signals based on Empirical Mode Decomposition," 2009 9th International Conference on Information Technology and Applications in Biomedicine, Larnaca, 2009, pp. 1-4.*

(Continued)

*Primary Examiner* — Hirdepal Singh
*Assistant Examiner* — Amneet Singh
(74) *Attorney, Agent, or Firm* — Jianq Chyun IP Office

(57) ABSTRACT

A signal decomposition method and an electronic apparatus using the same are proposed. The method includes the following steps: retrieving a first signal; performing a deterministic filtering operation to the first signal to decompose the first signal into at least one primary signal, where the at least one primary signal includes a second signal having a constant trend; and performing a non-deterministic filtering operation to the second signal to decompose the second signal into at least one secondary signal, where one of the at least one secondary signal has the constant trend and a sum of the at least one primary signal and the at least one secondary signal is the first signal.

10 Claims, 6 Drawing Sheets

(56) References Cited

U.S. PATENT DOCUMENTS

| | | | | |
|---|---|---|---|---|
| 2003/0033094 A1* | 2/2003 | Huang | ............... | G06F 17/14 702/39 |
| 2004/0078160 A1* | 4/2004 | Frei | ............... | G06F 17/14 702/79 |
| 2007/0073120 A1* | 3/2007 | Li | ............... | G06K 9/00503 600/323 |
| 2008/0027341 A1* | 1/2008 | Sackner | ............... | A61B 5/0205 600/509 |
| 2008/0065337 A1* | 3/2008 | Huang | ............... | G06F 17/14 702/66 |
| 2008/0167569 A1* | 7/2008 | Ermes | ............... | A61B 5/0476 600/544 |
| 2009/0326419 A1* | 12/2009 | Gonzalez Rojas | ............... | A61B 5/1101 600/587 |
| 2010/0092028 A1* | 4/2010 | Huang | ............... | G06F 17/14 382/100 |
| 2010/0179974 A1* | 7/2010 | Pao | ............... | G06F 17/14 708/207 |
| 2011/0015532 A1* | 1/2011 | Koertge | ............... | A61B 5/0402 600/509 |
| 2013/0190638 A1* | 7/2013 | Chon | ............... | A61B 5/0404 600/521 |
| 2013/0282339 A1* | 10/2013 | Ricci | ............... | G06K 9/00523 702/190 |
| 2014/0064527 A1 | 3/2014 | Walther et al. | | |
| 2014/0228701 A1* | 8/2014 | Chizeck | ............... | A61B 5/04012 600/544 |
| 2015/0162009 A1* | 6/2015 | Huang | ............... | A61B 5/7275 704/205 |

OTHER PUBLICATIONS

Norden E. Huang, et al., "The empirical mode decomposition and the Hilbert spectrum for nonlinear and non-stationary time series analysis," Proceedings of The Royal Society A: Mathematical, Physical and Engineering Sciences, vol. 454, No. 1971, Mar. 8, 1998, pp. 903-pp. 995.

Patrick Flandrin, et al., "Empirical Mode Decomposition as a Filter Bank," Signal Processing Letters, IEEE, vol. 11, No. 2, Feb. 2004 , pp. 112-pp. 114.

R. Balocchi, et al., "Deriving the respiratory sinus arrhythmia from the heartbeat time series using empirical mode decomposition," Chaos, Solitons & Fractals, vol. 20, Issue 1, Apr. 2004, pp. 171-pp. 177.

Zhaohua Wu, et al., "Ensemble Empirical Mode Decomposition: A Noise Assisted Data Analysis Method," Advances in Adaptive Data Analysis, vol. 1, Issue 1, Jan. 2009.

Jia-Rong Yeh, et al., "Complementary Ensemble Empirical Mode Decomposition: A Novel Noise Enhanced Data Analysis Method," Advances in Adaptive Data Analysis, vol. 2, Issue 2, Apr. 2010.

Alexandros Karagiannis, et al., "Noise-Assisted Data Processing With Empirical Mode Decomposition in Biomedical Signals," IEEE Transactions on Information Technology in Biomedicine, vol. 15, No. 1, Nov. 11, 2010, pp. 11-pp. 18.

Ching-Shuen Chen, et al., "Ensemble Empirical Mode Decomposition for Atherosclerosis in High-Risk Subjects," Communications and Signal Processing (ICICS) 2011 8th International Conference on Information, Dec. 13-16, 2011, pp. 1-pp. 4.

Sheng-Chi Kao, et al., "Reflection Wave Analysis Based on Ensemble Empirical Mode Decomposition," E-Health and Bioengineering Conference (EHB), Nov. 21-23, 2013, pp. 1-pp. 4.

Basic ECG Interpretation Tutorial, Section 12: ECG Artifacts—Muscle tremor / noise, retrieved on Jun. 16, 2016, available at: http://www.mauvila.com/images/Tremor.gif.

Technical Problems—ECGpedia, retrieved on Jun. 16, 2016, available at: http://www.wikidoc.org/images/5/5e/BaselineDrift.png.

Basic ECG Interpretation Review—Artifact, retrieved on Jun. 16, 2016, available at: http://ecgreview.weebly.com/uploads/1/6/4/7/16474710/2645140_orig.jpg.

The University of Nottingham, Divisional of Nursing, Practice Learning, Cardiology Teaching Package, Types and Causes of Interferancen—Artefact, retrieved on Jun. 16, 2016, available at: http://www.nottingham.ac.uk/nursing/practice/resources/cardiology/images/artifact_1.gif.

* cited by examiner

SIGNAL DECOMPOSITION METHOD AND ELECTRONIC APPARATUS USING THE SAME

CROSS-REFERENCE TO RELATED APPLICATION

This application claims the priority benefit of Taiwan application serial no. 104107944, filed on Mar. 12, 2015. The entirety of the above-mentioned patent application is hereby incorporated by reference herein and made a part of this specification.

BACKGROUND OF THE INVENTION

1. Field of the Invention

The invention relates to a signal decomposition method and an electronic apparatus using the same.

2. Description of Related Art

While a variety of algorithms (e.g., Fourier transform, wavelet transform, s-transform, z-transform, empirical mode decomposition (EMD), ensemble empirical mode decomposition (EEMD), etc.,) are available in the conventional technologies to decompose signals, these algorithms are not very applicable due to their inherent limitations.

For example, algorithms such as Fourier transform, s-transform, and z-transform inherently involve the concept of infinite series. Therefore, it is difficult to put these algorithms into practice with a limited number of circuits. In other words, there may be distortion to a certain extent if these algorithms are used to decompose signals.

Also, taking EMD as another example, even though EMD improves the performance of analyzing non-stationary signals and non-linear signals, the issue of mode mixing may occur when EMD is carried out. Thus, the applicability of EMD is influenced. As for EEMD, even though EEMD may introduce noises into a first signal to be decomposed to improve the fluctuations of non-stationary characteristics, so as to decompose the first signal into a plurality of intrinsic mode functions (IMF), EEMD requires to massively perform non-deterministic filtering operations (e.g., cubic spline interpolation) recursively, making the computation and time for computation required by EEMD significantly higher. Thus, EEMD is not very applicable.

SUMMARY OF THE INVENTION

Accordingly, the invention provides a signal decomposition method and an electronic apparatus using the same. The signal decomposition method and the electronic apparatus using the same sequentially performs a deterministic filtering operation and a non-deterministic filtering operation to a first signal to be decomposed, so as to decompose a signal without distortion with a lower computation load and shorter computation time.

The invention provides a signal decomposition method, suitable for an electronic apparatus. The method includes steps as follows: retrieving a first signal; performing a deterministic filtering operation to the first signal to decompose the first signal into at least one primary signal, wherein the at least one primary signal includes a second signal having a constant trend; and performing a non-deterministic filtering operation to the second signal to decompose the second signal into at least one secondary signal, wherein one of the at least one secondary signal has the constant trend, and a sum of the at least one primary signal and the at least one secondary signal is the first signal.

According to an embodiment of the invention, the step that the first signal performs the deterministic filtering operation to decompose the first signal into the at least one primary signal includes: detrending the first signal based on a deterministic filtering algorithm to obtain one of the at least one primary signal; determining whether the one of the at least one primary signal has the constant trend; and defining the one of the at least one primary signal as the second signal when the one of the at least one primary signal has the constant trend.

According to an embodiment of the invention, when the one of the at least one primary signal does not have the constant trend, the one of the at least one primary signal is defined as the first signal, and the first signal is detrended again based on the deterministic filtering algorithm to obtain another of the at least one primary signal.

According to an embodiment of the invention, the step of detrending the first signal based on the deterministic filtering algorithm to obtain the one of the at least one primary signal includes: retrieving a trend signal of the first signal based on the deterministic filtering algorithm; and subtracting the trend signal from the first signal to obtain the one of the at least one primary signal.

According to an embodiment of the invention, the step of performing the non-deterministic filtering operation to the second signal to decompose the second signal into the at least one secondary signal includes: detrending the second signal based on a non-deterministic filtering algorithm to obtain one of the at least one secondary signal; determining whether the one of the at least one secondary signal has the constant trend; and defining the one of the at least one secondary signal as the second signal when the one of the at least one secondary signal does not have the constant trend, and detrending the second signal again based on the non-deterministic filtering algorithm to obtain another of the at least one secondary signal.

According to an embodiment of the invention, when the one of the at least one secondary signal has the constant trend, the at least one primary signal and the at least one secondary signal are recorded.

According to an embodiment of the invention, the step of detrending the second signal based on the non-deterministic filtering algorithm to obtain the one of the at least one secondary signal includes: retrieving a trend signal of the second signal based on the non-deterministic filtering algorithm; and subtracting the trend signal from the second signal to obtain the one of the at least one secondary signal.

The invention provides an electronic apparatus, including a storage unit and a processing unit. The storage unit includes a plurality of modules. The processing unit is coupled to the storage unit and accesses and executes the modules. The modules include a retrieving module, a first filter module, and a second filter module. The retrieving module retrieves a first signal. The first filter module performs a deterministic filtering operation to the first signal to decompose the first signal into at least one primary signal. In addition, the at least one primary signal includes a second signal having a constant trend. The second filter module performs a non-deterministic filtering operation to the second signal to decompose the second signal into at least one secondary signal. Moreover, one of the at least one secondary signal has the constant trend, and a sum of the at least one primary signal and the at least one secondary signal is the first signal.

According to an embodiment of the invention, the first filter module is configured to detrend the first signal based on a deterministic filtering algorithm to obtain one of the at least one primary signal, determine whether the one of the at least one primary signal has the constant trend, and define the one of the at least one primary signal as the second signal when the one of the at least one primary signal has the constant trend.

According to an embodiment of the invention, when the one of the at least one primary signal does not have the constant trend, the first filter module is configured to define the one of the at least one primary signal as the first signal, and the first signal is detrended again based on the deterministic filtering algorithm to obtain another of the at least one primary signal.

According to an embodiment of the invention, the first filter module is configured to retrieve a trend signal of the second signal based on the non-deterministic filtering algorithm and subtract the trend signal from the first signal to obtain the one of the at least one primary signal.

According to an embodiment of the invention, the second filter module is configured to detrend the second signal based on a non-deterministic filtering algorithm to obtain one of the at least one secondary signal, determine whether the one of the at least one secondary signal has the constant trend, and define the one of the at least one secondary signal as the second signal when the one of the at least one secondary signal does not have the constant trend, and detrend the second signal again based on the non-deterministic filtering algorithm to obtain another of the at least one secondary signal.

According to an embodiment of the invention, when the one of the at least one secondary signal has the constant trend, the second filter module is configured to record the at least one primary signal and the at least one secondary signal.

According to an embodiment of the invention, the second filter module is configured to retrieve a trend signal of the second signal based on the non-deterministic filtering algorithm, and subtract the trend signal from the second signal to obtain the one of the at least one secondary signal.

Based on above, the signal decomposition method and the electronic apparatus using the same according to the embodiments of the invention may recursively detrend the first signal into the at least one primary signal by using the deterministic filtering operation. When the primary signal having a constant (i.e., the second signal) trend is found, the signal decomposition and the electronic apparatus using the same according to the embodiments of the invention may recursively detrend the second signal into the at least one secondary signal by using the non-deterministic filtering operation.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
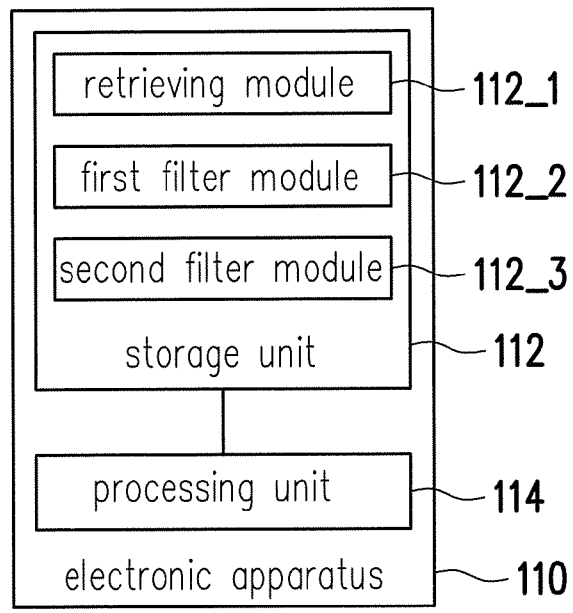
FIG. 1 is a schematic view illustrating an electronic apparatus according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a schematic view illustrating an electronic apparatus according to an embodiment of the invention. An electronic apparatus 100 is, for example, a medical instrument measuring a variety of stationary and non-stationary physiological signals (e.g., blood pressure, respiration, brain waves, electrocardiographic signals, etc.,) for medical staffs reference. The medical instrument may include a display displaying the physiological data and a user interface unit (e.g., button and touch screen, etc.,) for the medical staff to operate, for example. In addition, the electronic apparatus 100 may also be a personal computer, work station, server, smart phone, tablet computer, or laptop, etc., that processes the physiological signals.

The electronic apparatus 100 includes a storage unit 112 and a processing unit 114. The storage unit 112 may be a memory, a hard drive, or any component that stores data. Also, the storage unit 112 may record a plurality of programming codes or modules. The processing unit 114 may be a general purpose process, a special purpose process, a digital signal processor, a plurality of microprocessors, one or more microprocessors combined with a digital signal processing core, a controller, a microcontroller, an application specific integrated circuit (ASIC), a field programmable gate array (FPGA), integrated circuits, state machines, advanced RISC machine (ARM) processors of any kind and similar devices.

In this embodiment, the processing unit 114 may access and executes a retrieving module 112_1, a first filter module 112_2, and a second filter module 112_3 to perform a signal decomposition method according to the invention.

Figure 2:
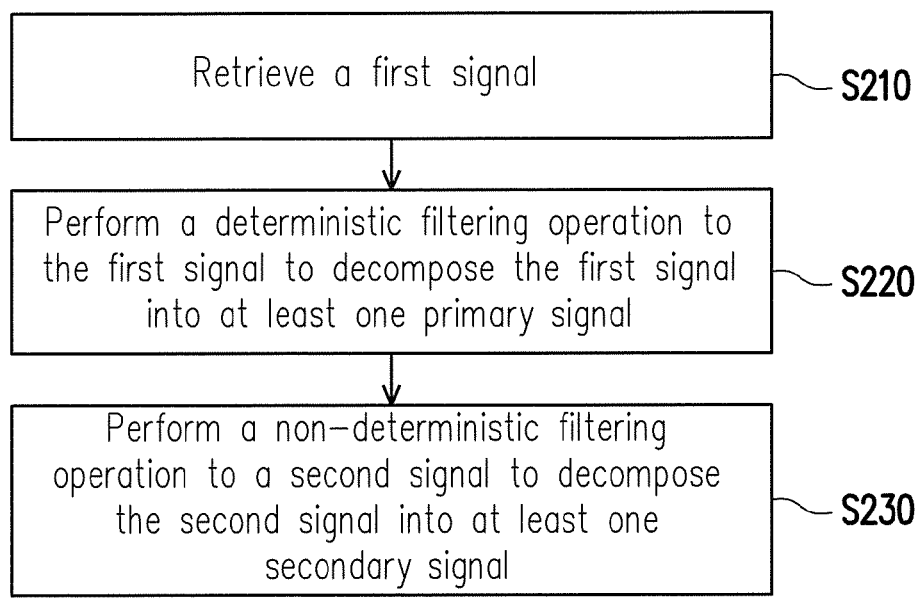
FIG. 2 is a flowchart illustrating a signal decomposition method according to an embodiment of the invention.

FIG. 2 is a flowchart illustrating a signal decomposition method according to an embodiment of the invention. The method provided in this embodiment may be performed by the electronic apparatus 100 shown in FIG. 1. In the following, the steps of the method of the embodiment are described in detail with reference to the components of FIG. 1.

At Step S210, the retrieving module 112_1 may retrieve a first signal. In an embodiment, the retrieving module 112_1 may control a variety of detection electrodes (not shown), probes (not shown), and other physiological signal measuring components disposed in the electronic apparatus 100 to measure a variety of physiological signals of the user as the first signal. In other embodiments, the retrieving module 112_1 may also access existing physiological signals from the storage unit 112 or other similar storage components and use the existing physiological signals as the first signal. However, the embodiments of the invention are not limited thereto.

At Step S220, the first filter module 112_2 may perform a deterministic filtering operation to the first signal to decompose the first signal into at least one primary signal. In an embodiment, the first filter module 112_2 may recursively detrend the first signal based on some deterministic filtering algorithms to individually obtain the at least one primary signal. In addition, when the first filter module 112_2 obtains the primary signal having a constant trend, the first filter module 112_2 may define the primary signal as a second signal.

Then, at Step S230, the second filter module 112_3 may perform a non-deterministic filtering operation to the second signal to decompose the second signal into at least one secondary signal.

In an embodiment, the second filter module 112_3 may recursively detrend the second signal based on some non-deterministic filtering algorithms to individually obtain the at least one secondary signal until the second filter module 112_3 obtain the secondary signal having a constant trend. To describe the details of Steps S220 and S230 more clearly, FIG. 3 is provided in the following for further description.

Figure 3:
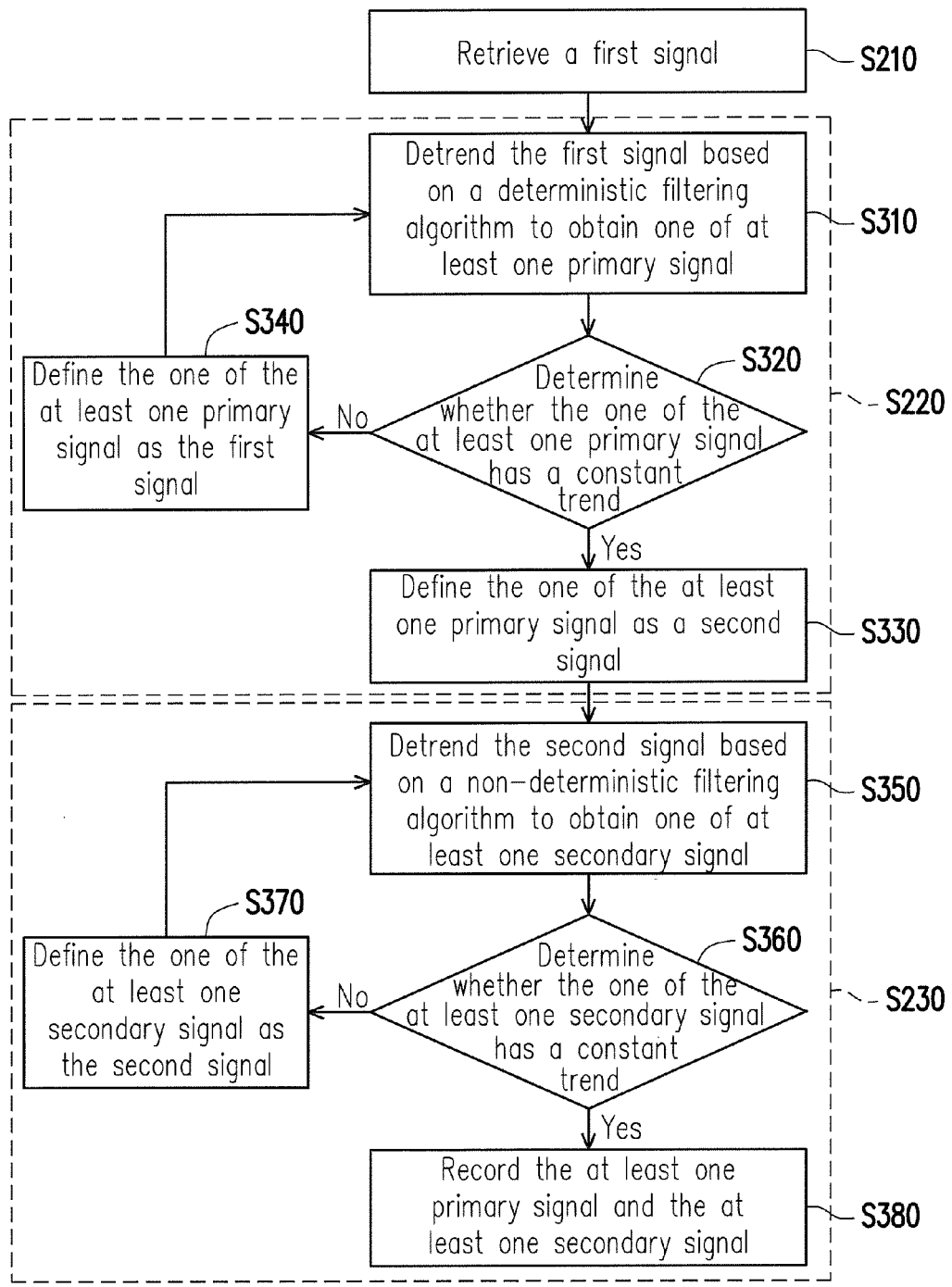
FIG. 3 is a flowchart illustrating the signal decomposition method shown in FIG. 2.

FIG. 3 is a flowchart illustrating the signal decomposition method shown in FIG. 2. In this embodiment, details concerning Step S210 may be referred to the description of FIG. 2, and are thus not repeated in the following. Also, Steps S220 and S230 of FIG. 2 are respectively divided into Steps S310 to S340 and Steps S350 to S380 shown in FIG. 3.

After Step S210, the first filter module 112_2 may detrend the first signal to obtain one of the at least one primary signal based on the deterministic filtering algorithm at Step S310. The deterministic filtering algorithm includes moving average (MA), low pass filtering, and partial regularized least squares (PRLS), etc., for example. However, the embodiments of the invention are not limited thereto. In an embodiment, the first filter module 112_2 may retrieve a trend signal of the first signal based on the deterministic filtering algorithm, and subtract the trend signal from the first signal to obtain the primary signal (i.e., the detrended first signal).

Then, at Step S320, the first filter module 112_2 may determine whether the one of the at least one primary signal (i.e., the detrended first signal) has a constant trend. In an embodiment, the first filter module 112_2 may determine whether the trend of the detrended first signal is constant based on, for example, statistical properties such as the mean value, amplitude ratio, etc., of the detrended first signal.

If the one of the at least one primary signal has a constant trend, the first filter module 112_2 may proceed to perform Step S330 to define the one of the at least one primary signal as the second signal. Then, the second filter module 112_3 may perform Steps S350 to S380 based on the second signal, so as to decompose the second signal into the at least one secondary signal based on the non-deterministic filtering operation.

Alternatively, if the one of the at least one primary signal does not have a constant trend, the first filter module 112_2 may proceed to perform Step S340 to define the one of the at least one primary signal as the first signal. Then, the first filter module 112_2 may repeat Steps S310, S320, and S340, so as to recursively detrend the redefined first signal until the primary signal having a constant trend is found.

At Step S350, the second filter module 112_3 may detrend the second signal based on the non-deterministic filtering algorithm to obtain one of the at least one secondary signal. The non-deterministic filtering algorithm includes cubic spline interpolation and other similar interpolation/extrapolation algorithms, for example. However, the embodiments of the invention are not limited thereto. In an embodiment, the second filter module 112_3 may retrieve a trend signal of the second signal based on the non-deterministic filtering algorithm, and subtract the trend signal from the second signal to obtain the secondary signal (i.e., the detrended second signal).

Then, at Step S360, the second filter module 112_3 may determine whether the one of the at least one secondary signal (i.e., the detrended second signal) has a constant trend. In an embodiment, the second filter module 112_3 may similarly determine whether the trend of the detrended second signal is constant based on statistical properties such as the mean value, amplitude ratio, etc., of the detrended second signal.

If the one of the at least one secondary signal does not have a constant trend, the second filter module 112_3 may proceed to perform Step S370 to define the one of the at least one secondary signal as the second signal. Then, the second filter module 112_3 may repeat Steps S350 to S370, so as to recursively detrend the redefined second signal until the secondary signal having a constant trend is found.

Alternatively, if the one of the at least one secondary signal has a constant trend, the second filter module 112_3 may proceed to perform Step S380 to record the at least one primary signal and the at least one secondary signal. In an embodiment, the at least one primary signal and the at least one secondary signal may respectively be, for example, intrinsic mode functions (IMF) corresponding to different time scales. Also, a sum of the at least one primary signal and the at least one secondary signal is equivalent to the first signal retrieved by the retrieving module 112_1 at Step S210.

In other embodiments, the electronic apparatus 100 may further provide the at least one primary signal and the at least one secondary signal to be recorded for the reference of relevant medical staff or the user, so that the medical staff or the user may conduct a signal analysis or make an interpretation about illness based on the IMF as required. However, the embodiments of the invention are not limited thereto.

In brief, the signal decomposition method according to the embodiments of the invention may be roughly divided into the deterministic filtering operation at a first stage and the non-deterministic filtering operation at a second stage. At the first stage, the method of the invention may recursively detrend the first signal based on the deterministic filtering algorithm (e.g., MA) so as to find the primary signal (i.e., the second signal) that makes the non-deterministic filtering operation at the second stage promptly converge. In this way, even though detrending of the second signal relies on the non-deterministic filtering operation (e.g., cubic spline interpolation) requiring more computation in the second stage, it does not require many times of recursion to find the respective secondary signals, so as to complete the signal decomposition operation of the first signal.

Moreover, based on results of validation through numerical values provided in the embodiments shown in FIGS. 4A to 4B and 5A to 5B in the following, the signal decomposition method provided in the invention has a shorter computation time than an ensemble empirical mode decomposition (EEMD) operation that uses the non-deterministic filtering operation throughout the operation. Thus, the signal decomposition method of the invention has a preferable practicality.

Figure 4A:
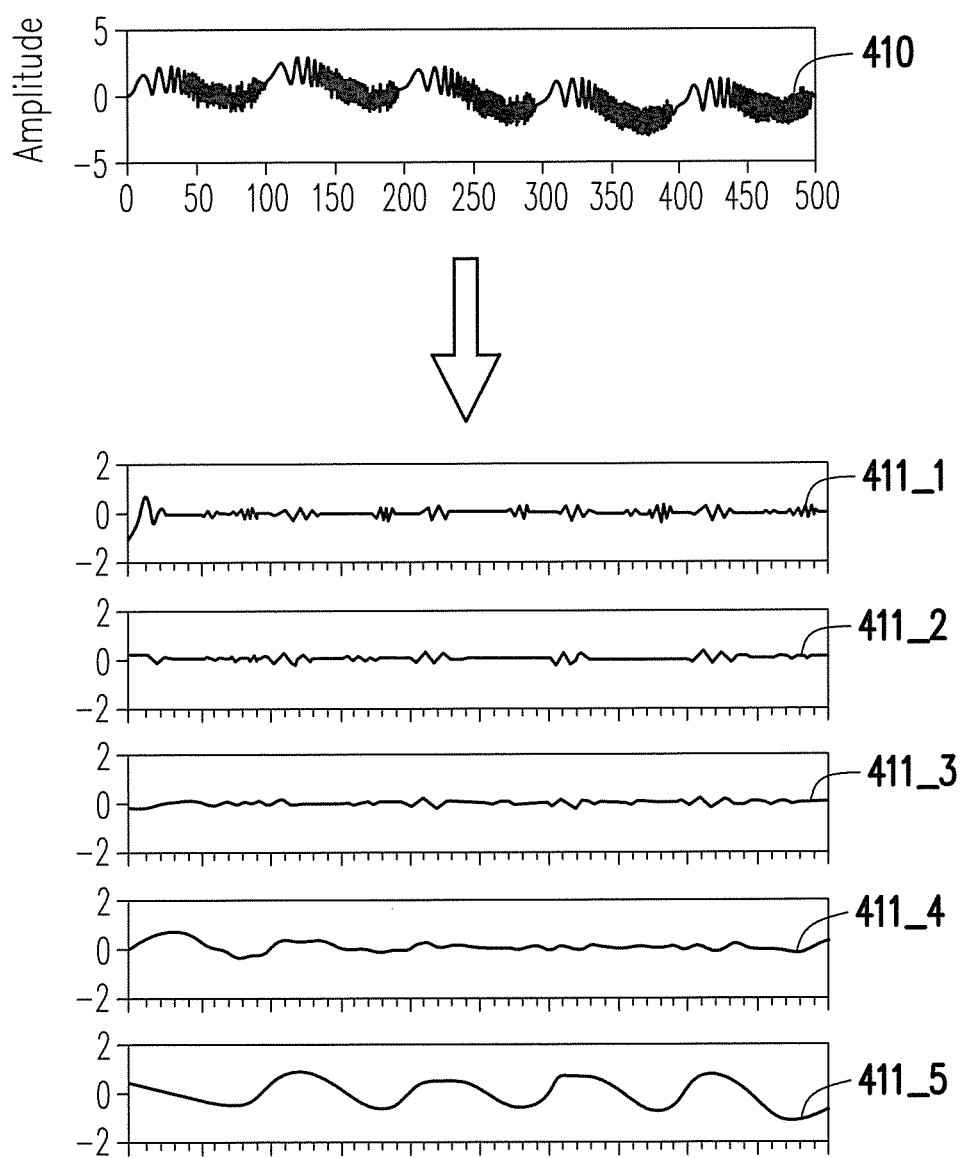
FIG. 4A is a schematic view illustrating decomposing a first signal according to an embodiment of the invention.

Referring to FIG. 4A, FIG. 4A is a schematic view illustrating decomposing a first signal according to an embodiment of the invention. In this embodiment, a first signal 410 may be decomposed into IMFs 411_1 to 411_5 according to the signal decomposition method of the invention or EEMD.

Figure 4B:
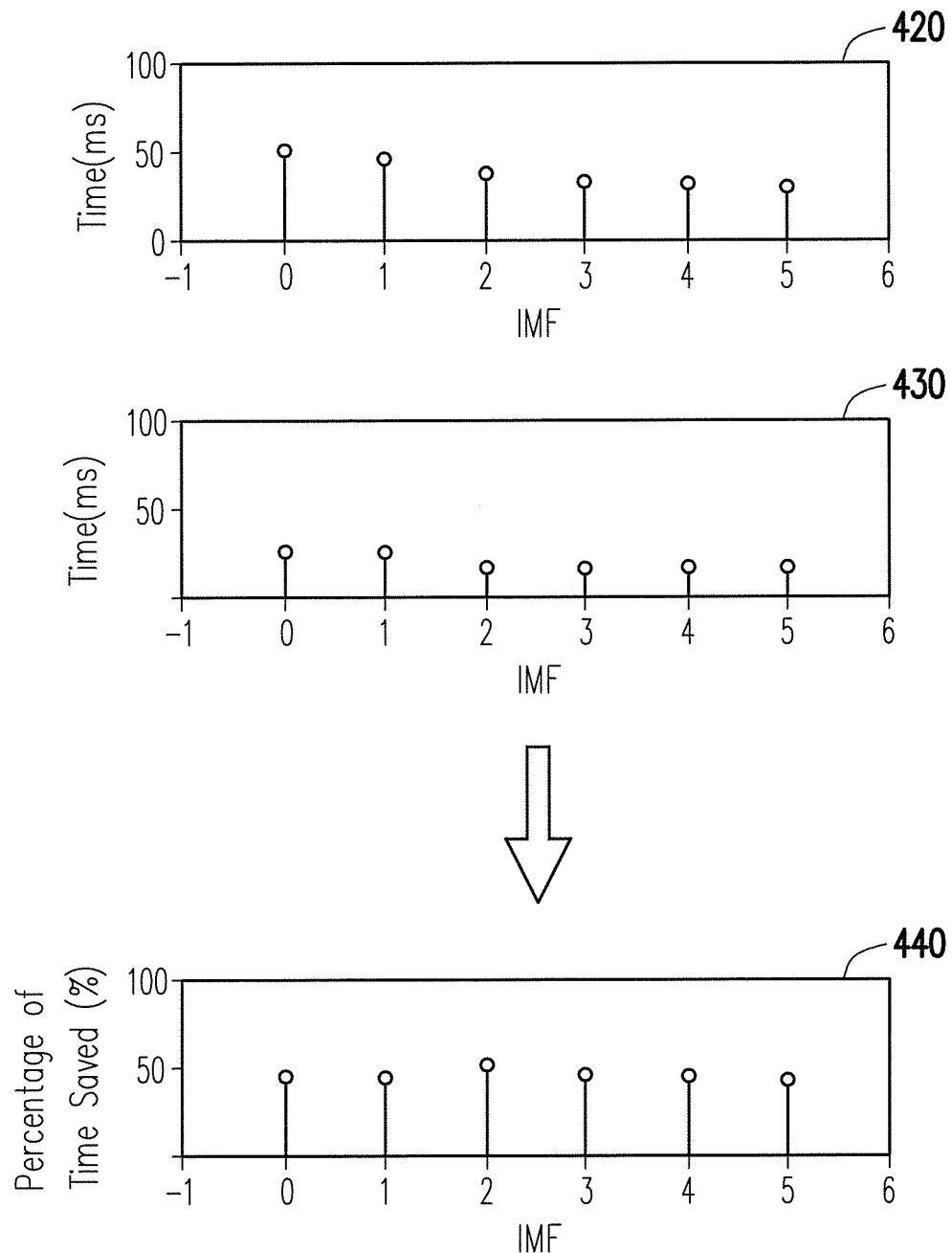
FIG. 4B is a view illustrating a comparison of computation time according to the embodiment shown in FIG. 4A.

Referring to FIG. 4B, FIG. 4B is a view illustrating a comparison of computation time according to the embodiment shown in FIG. 4A. In this embodiment, a table 420 illustrates the time required to respectively obtain the IMFs 411_1 to 411_5 included in the first signal 410 based on EEMD, and a table 430 illustrates the time required to respectively obtain the IMFs 411_1 to 411_5 included in the first signal 410 based on the signal decomposition method according to the invention. A table 440 illustrates percentages of time saved by the table 430 as compared to the table 420.

As shown in the table 440, the time required to find the IMFs 411_1 to 411_5 based on the method according to the invention is only about 50% of the time required to find the IMFs 411_1 to 411_5 based on EEMD. In other words, the method provided in the invention requires a shorter time for computation than the time required by EEMD.

Figure 5A:
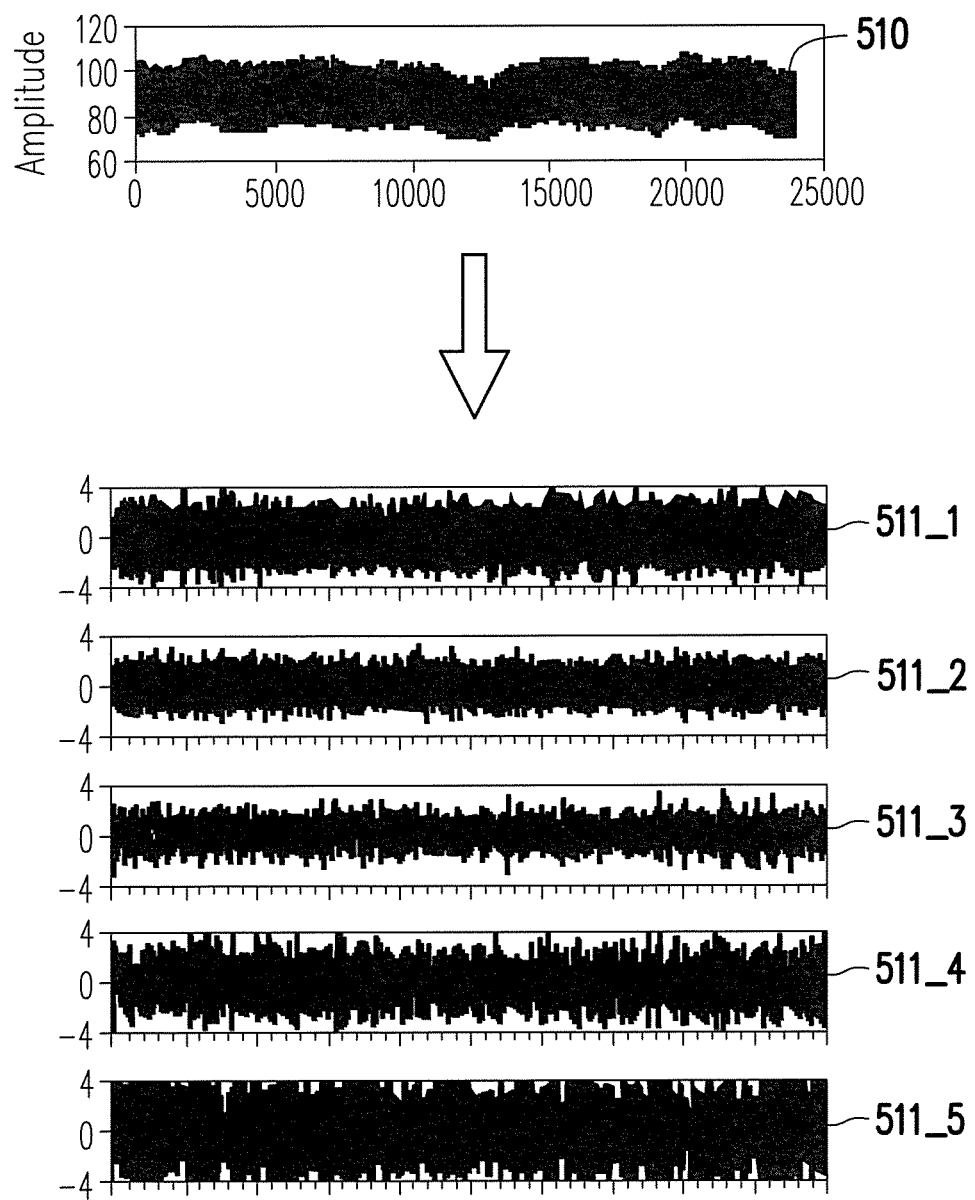
FIG. 5A is a schematic view illustrating decomposing a first signal according to an embodiment of the invention.

Referring to FIG. 5A, FIG. 5A is a schematic view illustrating decomposing a first signal according to an embodiment of the invention. In this embodiment, a first signal 510 is an arterial blood pressure signal, for example, and the first signal 510 may be decomposed into IMFs 511_1 to 511_5 according to the signal decomposition method according to the invention or EEMD.

Figure 5B:
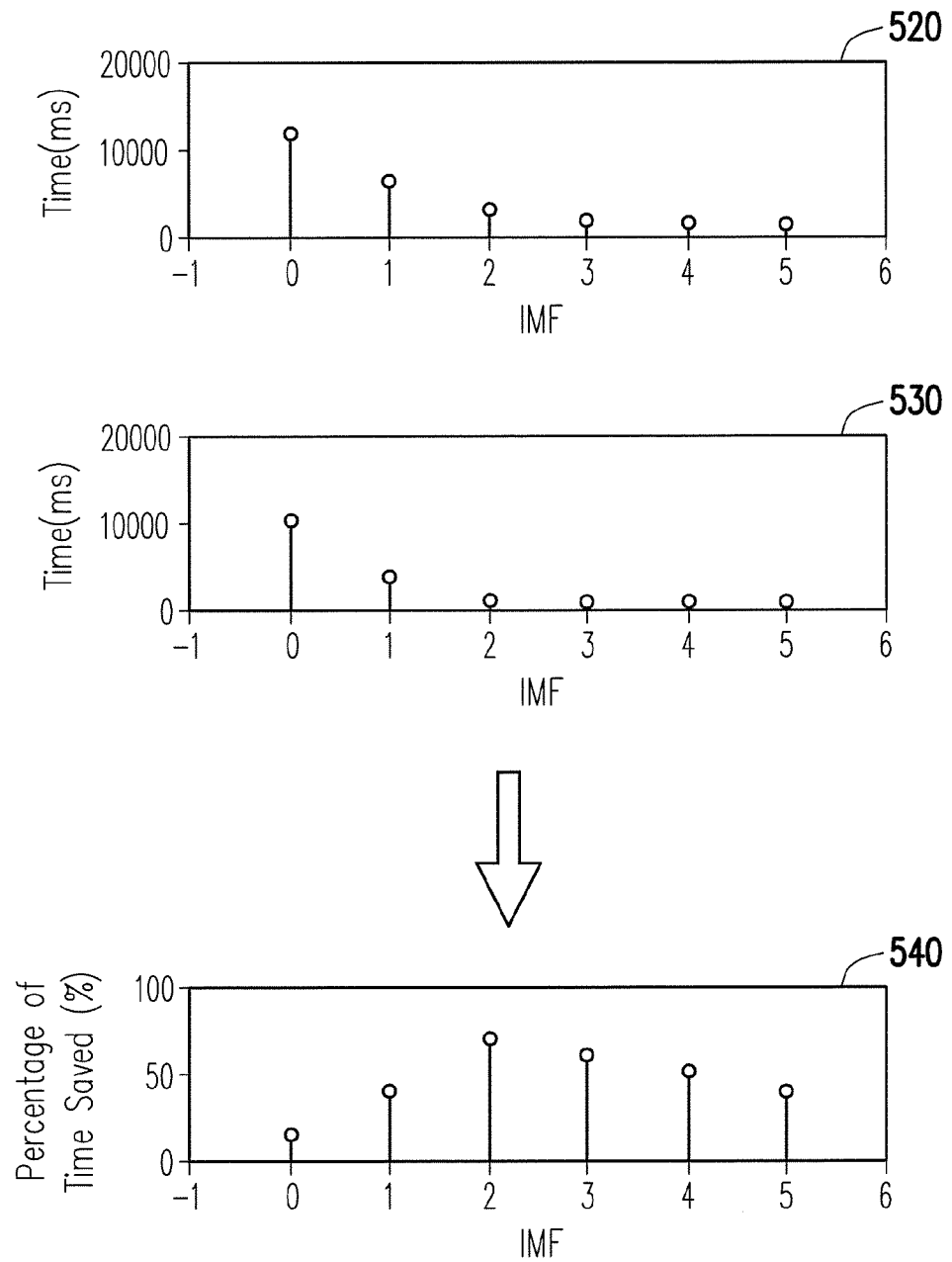
FIG. 5B is a view illustrating a comparison of computation time according to the embodiment shown in FIG. 5A.

Referring to FIG. 5B, FIG. 5B is a view illustrating a comparison of computation time according to the embodiment shown in FIG. 5A. In this embodiment, a table 520 illustrates the time required to respectively obtain the IMFs 511_1 to 511_5 included in the first signal 510 based on EEMD, and a table 530 illustrates the time required to respectively retrieve the IMFs 511_1 to 511_5 included in the first signal 510 based on the signal decomposition method according to the invention. A table 540 illustrates percentages of time saved by the table 530 as compared to the table 520.

As shown in the table 540, the time required to find the IMFs 511_1 to 511_5 based on the method according to the invention remains less than the time required to find the IMFs 511_1 to 511_5 based on EEMD. In other words, FIG. 5B again shows that the method provided in the invention requires a shorter time for computation than the time required by EEMD.

In view of the foregoing, the signal decomposition method and the electronic apparatus using the same according to the embodiments of the invention may recursively detrend the first signal into the at least one primary signal by using the deterministic filtering operation in the first stage. When the primary signal having a constant trend (i.e., the second signal) is found, the signal decomposition and the electronic apparatus using the same according to the embodiments of the invention may recursively detrend the second signal into the at least one secondary signal by using the non-deterministic filtering operation in the second stage. Since the second signal found in the first stage is very close to a converging interval of the second stage, the number of times of recursion in the second stage may be reduced. In addition, the results of validation through numerical values also show that the signal decomposition method and the electronic apparatus using the same according to the embodiments of the invention have a shorter computation time and consequently a higher applicability.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A signal decomposition method, adapted to an electronic apparatus which has a processor, comprising:
   retrieving a first signal by the processor executing a retrieving module;
   performing a deterministic filtering operation to the first signal to decompose the first signal into at least one primary signal by the processor executing a first filter module, wherein the at least one primary signal comprises a second signal having a constant trend; and
   performing a non-deterministic filtering operation to the second signal to decompose the second signal into at least one secondary signal by the processor executing a second filter module, wherein one of the at least one secondary signal has the constant trend, and a sum of the at least one primary signal and the at least one secondary signal is the first signal,
   wherein the step that performs the deterministic filtering operation to decompose the first signal into the at least one primary signal comprises:
      detrending the first signal based on a deterministic filtering algorithm to obtain one of the at least one primary signal;
      determining whether the one of the at least one primary signal has the constant trend; and
      when the one of the at least one primary signal has the constant trend, defining the one of the at least one primary signal as the second signal,
      when the one of the at least one primary signal does not have the constant trend, the one of the at least one primary signal is defined as the first signal, and detrending the first signal is again based on the deterministic filtering algorithm to obtain another of the at least one primary signal.

2. The method as claimed in claim 1, wherein the step of detrending the first signal based on the deterministic filtering algorithm to obtain the one of the at least one primary signal comprises:
   retrieving a trend signal of the first signal based on the deterministic filtering algorithm; and
   subtracting the trend signal from the first signal to obtain the one of the at least one primary signal.

3. The method as claimed in claim 1, wherein the step of performing the non-deterministic filtering operation to the second signal to decompose the second signal into the at least one secondary signal comprises:
   detrending the second signal based on a non-deterministic filtering algorithm to obtain one of the at least one secondary signal;
   determining whether the one of the at least one secondary signal has the constant trend; and
   when the one of the at least one secondary signal does not have the constant trend, defining the one of the at least one secondary signal as the second signal, and detrending the second signal again based on the non-deterministic filtering algorithm to obtain another of the at least one secondary signal.

4. The method as claimed in claim 3, wherein when the one of the at least one secondary signal has the constant trend, the at least one primary signal and the at least one secondary signal are recorded.

5. The method as claimed in claim 3, wherein the step of detrending the second signal based on the non-deterministic filtering algorithm to obtain the one of the at least one secondary signal comprises:
   retrieving a trend signal of the second signal based on the non-deterministic filtering algorithm; and
   subtracting the trend signal from the second signal to obtain the one of the at least one secondary signal.

6. An electronic apparatus, comprising:
   a storage device, storing a plurality of modules;
   a processor, coupled to the storage device and accessing and executing the modules, wherein the modules comprise:
      a retrieving module, retrieving a first signal;
      a first filter module, performing a deterministic filtering operation to the first signal to decompose the first signal into at least one primary signal, wherein the at least one primary signal comprises a second signal having a constant trend; and
      a second filter module, performing a non-deterministic filtering operation to the second signal to decompose the second signal into at least one secondary signal, wherein one of the at least one secondary signal has the constant trend, and a sum of the at least one primary signal and the at least one secondary signal is the first signal,
   wherein the first filter module is configured to:
      detrend the first signal based on a deterministic filtering algorithm to obtain one of the at least one primary signal;
      determine whether the one of the at least one primary signal has the constant trend; and
      define the one of the at least one primary signal as the second signal when the one of the at least one primary signal has the constant trend,
      when the one of the at least one primary signal does not have the constant trend, the first filter module is configured to define the one of the at least one primary signal as the first signal, and detrend the first signal again based on the deterministic filtering algorithm to obtain another of the at least one primary signal.

7. The electronic apparatus as claimed in claim 6, wherein the first filter module is configured to:
   retrieve a trend signal of the first signal based on the deterministic filtering algorithm; and
   subtract the trend signal from the first signal to obtain the one of the at least one primary signal.

8. The electronic apparatus as claimed in claim 6, wherein the second filter module is configured to:
   detrend the second signal based on a non-deterministic filtering algorithm to obtain one of the at least one secondary signal;
   deteimine whether the one of the at least one secondary signal has the constant trend; and
   define the one of the at least one secondary signal as the second signal when the one of the at least one secondary signal does not have the constant trend, and detrend the second signal again based on the non-deterministic filtering algorithm to obtain another of the at least one secondary signal.

9. The electronic apparatus as claimed in claim 8, wherein when the one of the at least one secondary signal has the constant trend, the second filter module is configured to record the at least one primary signal and the at least one secondary signal.

10. The electronic apparatus as claimed in claim 8, wherein the second filter module is configured to:
   retrieve a trend signal of the second signal based on the non-deterministic filtering algorithm; and
   subtract the trend signal from the second signal to obtain the one of the at least one secondary signal.

* * * * *